(12) United States Patent
Gu et al.

(10) Patent No.: US 9,470,650 B2
(45) Date of Patent: Oct. 18, 2016

(54) TWO-DIMENSIONAL ELECTRON GAS (2DEG)-BASED CHEMICAL SENSORS

(75) Inventors: Jason Gu, Pittsburgh, PA (US); Jacob H. Melby, Pittsburgh, PA (US); Robert F. Davis, Pittsburgh, PA (US)

(73) Assignee: Carnegie Mellon University, Pittsburgh, PA (US)

( * ) Notice: Subject to any disclaimer, the term of this patent is extended or adjusted under 35 U.S.C. 154(b) by 171 days.

(21) Appl. No.: 13/880,566

(22) PCT Filed: Oct. 20, 2011

(86) PCT No.: PCT/US2011/057014
§ 371 (c)(1),
(2), (4) Date: Apr. 19, 2013

(87) PCT Pub. No.: WO2012/054683
PCT Pub. Date: Apr. 26, 2012

(65) Prior Publication Data
US 2013/0288378 A1   Oct. 31, 2013

Related U.S. Application Data

(60) Provisional application No. 61/455,591, filed on Oct. 21, 2010, provisional application No. 61/465,094, filed on Mar. 14, 2011.

(51) Int. Cl.
*G01N 27/414* (2006.01)

(52) U.S. Cl.
CPC ........ *G01N 27/414* (2013.01); *G01N 27/4141* (2013.01)

(58) Field of Classification Search
CPC .................. G01N 27/414; G01N 27/4141
USPC ............. 73/23.2, 23.31, 25.01, 25.05, 31.05, 73/31.06
See application file for complete search history.

(56) References Cited

U.S. PATENT DOCUMENTS

| | | | |
|---|---|---|---|
| 5,834,627 A | * | 11/1998 | Ricco et al. ............... 73/23.31 |
| 7,361,946 B2 | | 4/2008 | Johnson et al. |
| 7,403,113 B2 | | 7/2008 | Moon et al. |
| 7,728,356 B2 | | 6/2010 | Suh et al. |

(Continued)

OTHER PUBLICATIONS

Schalwig, J., et al. "Gas sensitive GaN/AlGaN-heterostructures." Sensors and Actuators B: Chemical 87.3 (2002): 425-430.*

(Continued)

*Primary Examiner* — Lyle Alexander
*Assistant Examiner* — Robert Eom
(74) *Attorney, Agent, or Firm* — Downs Rachlin Martin PLLC

(57) ABSTRACT

Sensors for sensing/measuring one or more analytes in a chemical environment. Each sensor is based on a semiconductor structure having an interfacial region containing a two-dimensional electron gas (2DEG). A catalyst reactive to the analyte(s) is in contact with the semiconductor structure. Particles stripped from the analyte(s) by the catalyst passivate the surface of the semiconductor structure at the interface between the catalyst and the structure, thereby causing the charge density in the 2DEG proximate the catalyst to change. When this basic structure is incorporated into an electronic device, such as a high-electron-mobility transistor (HEMT) or a Schottky diode, the change in charge density manifests into a change in an electrical response of the device. For example, in an HEMT, the change in charge density manifests as a change in current through the transistor, and, in a Schottky diode, the change in charge density manifests as a change in capacitance.

9 Claims, 6 Drawing Sheets

(56) References Cited

U.S. PATENT DOCUMENTS

| | | | |
|---|---|---|---|
| 2002/0167023 A1 | 11/2002 | Chavarkar et al. | |
| 2003/0020092 A1 | 1/2003 | Parikh et al. | |
| 2004/0178082 A1* | 9/2004 | McDaniel et al. | 205/785.5 |
| 2008/0006845 A1 | 1/2008 | Derluyn et al. | |
| 2010/0170325 A1 | 7/2010 | Ren et al. | |

OTHER PUBLICATIONS

Song, Junghui, et al. "AlGaN/GaN Schottky diode hydrogen sensor performance at high temperatures with different catalytic metals." Solid-state electronics 49.8 (2005): 1330-1334.*

Anderson, T. J., et al. "Effect of bias voltage polarity on hydrogen sensing with AlGaN/GaN Schottky diodes." Applied Surface Science 255.5 (2008): 2524-2526.*

International Search Report and Written Opinion dated Apr. 27, 2012, issued in connection with related PCT/US2011/057014, filed Oct. 20, 2011.

Schalwig, J. et al.; Hydrogen Response Mechanism of Pt-GaN Schottky Diodes; Applied Physics Letters, vol. 80, No. 7, Feb. 18, 2002; pp. 1222-1224.

* cited by examiner

TWO-DIMENSIONAL ELECTRON GAS (2DEG)-BASED CHEMICAL SENSORS

RELATED APPLICATION DATA

This application claims the benefit of priority of U.S. Provisional Patent Application Ser. No. 61/455,591, filed on Oct. 21, 2010, and titled "Chemically Stable Sensor For Detecting Hydrogen In Severe Environments," and U.S. Provisional Patent Application Ser. No. 61/465,094, filed on Mar. 14, 2011, and titled "Chemically Stable Sensor For Detecting Hydrocarbons In Severe Environments," each of which is incorporated by reference herein in its entirety.

FIELD OF THE INVENTION

The present invention generally relates to the field of sensors for sensing and measuring the presence of chemical analytes. In particular, the present invention is directed to two-dimensional electron gas (2DEG)-based chemical sensors and associated methods, apparatuses, and systems.

BACKGROUND

Chemical sensors are significant due to their ability to optimize efficiency and/or ensure safety. In many industrial settings, harsh operational conditions prevent the deployment of such sensors into locations where safety hazards or operational inefficiencies originate. Given such deployments, many processes can be made safer and more efficient.

The presence of reactive substances and/or elevated temperatures and hydrogen in the same environment or enclosure can result in highly exothermic reactions that form products that can undergo further reactions with the materials present in the environment. An increase in temperature within such an environment exponentially increases the rate of reaction and therefore increases the possibility of explosion, which could result in workplace injury and/or facility destruction. Currently, no sensors appear to be suitable due to the severity of the environment, which causes rapid degradation of the materials used, leading to sensing failure.

Similarly, presence of reactive substances and molecules of hydrocarbon alkane gases, $C_xH_y$, in a common environment/enclosure can result in highly exothermic reactions that, under controlled conditions, serve as our main power source, but under uncontrolled conditions can result in explosions that cause workplace injury and facility destruction. In addition, the growing concerns regarding the coupled achievements of increased energy efficiency and reduced environmental degradation during the burning of hydrocarbon-based fossil fuels for power generation has led to a significant need for in-situ process monitoring of the concentrations of hydrocarbon gases. However, most sensors are incapable of in-situ process monitoring due to the inability to operate in either severe thermal environments, such as the elevated temperatures caused by the exothermic combustion reactions required for power generation, or in anaerobic and corrosive environments such as sea water that would be encountered during monitoring to detect the presence of hydrocarbons under the ocean floor and groundwater contamination from, e.g., fractures in shales, leading to release of natural gas.

SUMMARY OF THE DISCLOSURE

In one implementation, the present disclosure is directed to a method of sensing a constituent of a chemical environment. The method includes providing an electronic semiconductor-based device for sensing the constituent, wherein the electronic semiconductor-based device includes: semiconducting layers designed and configured to provide a two-dimensional electron gas (2DEG) at an interfacial region of the semiconducting layers; and a catalyst that is: selected to dissociate a component of the constituent from the constituent; and located between the semiconducting layers and the chemical environment such that the dissociated component of the constituent changes the mobility of electrons in the 2DEG; and measuring an electrical effect of the change in the mobility of electrons in the 2DEG so as to sense the constituent.

In another implementation, the present disclosure is directed to a method of sensing a constituent of a chemical environment, wherein the constituent is a member of a chemical family. The method includes providing an array of sensors designed and configured to sense multiple member chemicals of the chemical family and having differing sensitivities to differing ones of the multiple member chemicals based on sensor temperature; exposing the array to the chemical environment; operating differing sensors in the array at differing temperatures; sensing an electrical response of each sensor in the array during the operating so as to create a response matrix; and analyzing the response matrix so as to determine the presence of the constituent and distinguish the constituent from the rest of the multiple member chemicals.

In still another implementation, the present disclosure is directed to a sensor for sensing a constituent of a chemical environment. The sensor includes an electronic device that includes: semiconducting layers designed and configured to provide a two-dimensional electron gas (2DEG) at an interfacial region of the semiconducting layers; and a catalyst: made of a material selected for its ability to dissociate a component of the constituent from the constituent; and that, when the sensor is deployed into the chemical environment, is located between the semiconducting layers and the chemical environment such that the dissociated component of the constituent changes the mobility of electrons in the 2DEG; and measurement circuitry designed and configured to measure an electrical effect of the change in the mobility of electrons in the 2DEG so as to sense the constituent.

In yet another implementation, the present disclosure is directed to a sensor system for sensing a constituent of a chemical environment, wherein the constituent is a member of a chemical family. The sensor system includes an array of sensors designed and configured to sense multiple member chemicals of the chemical family and having differing sensitivities to differing ones of the multiple member chemicals based on sensor temperature; a temperature control system in thermal communication with the array and designed and configured to maintain differing ones of the sensors at differing temperatures during operation of the sensor system; a sensor response system operatively coupled to the sensors and designed and configured to measure responses of the sensors; and a constituent analysis system designed and configured to determine the presence of the constituent and distinguish the constituent from the rest of the multiple member chemicals.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

DETAILED DESCRIPTION

In one aspect, the present disclosure is directed to two-dimensional-electron-gas-based sensors for detecting and/or measuring the presence of one or more chemical analytes that are constituents of a chemical environment. Sensors disclosed herein are based on layered semiconductor structures that include interfacial regions designed to promote the formation of two-dimensional electron gas (2DEG) on the semiconductor surface or buried within the semiconductor stack. For any given layered semiconductor structure of the present disclosure, the charge density within the 2DEG is modified by the presence of certain particles (i.e. analyte) on an external surface of the layered structure that originate outside the structure. By selectively controlling the particles that reach an external surface of the layered semiconductor structure proximate to the 2DEG, the effect of the presence of those particles on charge density within the 2DEG can be leveraged to create a sensor that can sense one or more materials that contain the particles. A useful feature of various sensors of the present disclosure is that they can be configured and made of materials such that they can be deployed in hostile environments, such as environments that are chemically harsh, at extreme temperatures, explosive, etc., or any possible combination thereof. Details on the functioning of a sensor made in accordance with the present invention are described below, as are some specific instantiations of sensors. In other aspects, the present disclosure is directed to methods of sensing and/or measuring one or more constituents of a chemical environment, as well as apparatuses and systems that utilize one or more sensors of the present invention.

Basic Sensor Structure

Figure 1:
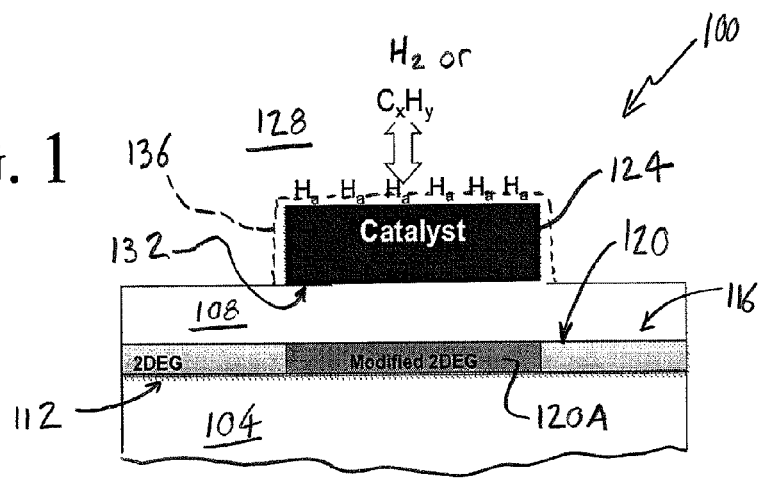
FIG. 1 is an elevational cross-sectional view of a two-dimensional electron gas (2DEG) sensor structure that illustrates the operating principles of a 2DEG sensor of the present disclosure.

Referring now to the drawings, FIG. 1 shows a layered semiconductor structure 100 used to illustrate the functioning of various sensors of the present invention. Hereinafter, for convenience, structure 100 is referred to as "basic sensor structure" for reasons that will become apparent upon reading this entire disclosure. Basic sensor structure 100 includes semiconducting layers, here first and second layers 104 and 108, that form a heterojunction 112 and are selected to provide an interfacial region 116 that contains a 2DEG 120. In the embodiment shown, layer 104 is a layer of a first undoped semiconductor material and layer 108 is a layer of second undoped semiconductor material that is different from the first undoped semiconductor material. In one example, first layer 104 is gallium nitride (GaN) and second layer 108 is an aluminum gallium nitride ($Al_xGa_{1-x}N$), wherein x=0.05 to 1.00. In another example, first layer 104 is $Al_xGa_{1-x}N$ and second layer 108 is $Al_yGa_{1-y}N$, wherein y>x. Gallium nitride based materials can be desirable for harsh environments due to their relative inertness and temperature stability. In other embodiments, it may be possible to user other materials.

Figure 2:
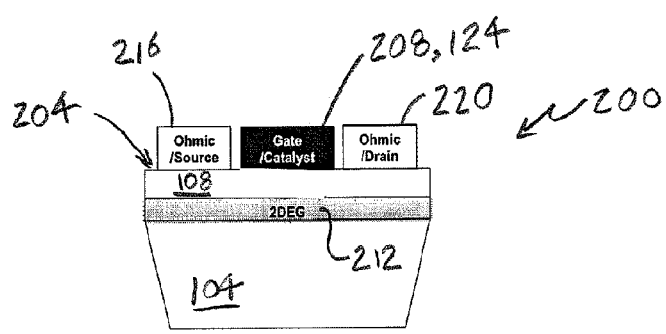
FIG. 2 is an elevational cross-sectional view of a sensor of the present disclosure based on a high-electron-mobility transistor (HEMT)
Figure 6:
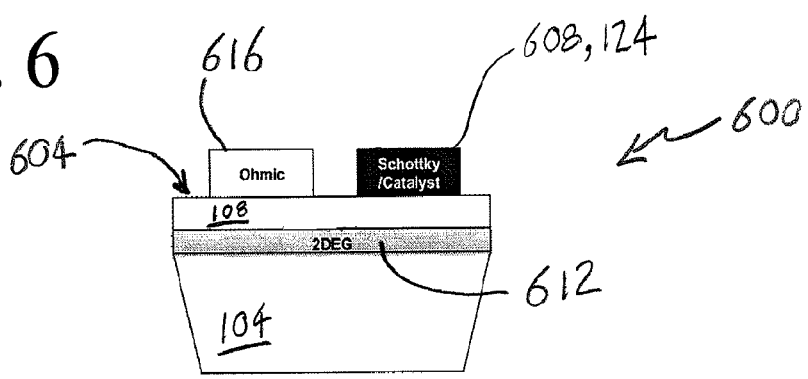
FIG. 6 is an elevational cross-sectional view of a sensor of the present disclosure based on a Schottky diode.

Basic sensor structure 100 also includes a catalyst 124 located on second layer 108. Catalyst 124 functions to decompose one or more constituents in an environment 128 to which the catalyst is exposed so as to allow certain particles from the decomposed constituent(s) to reach the interface 132 of the catalyst with second layer 108. When those particles are present at interface 132, they modify the interfacial states present, which in turn modify the charge density within 2DEG 120 in the vicinity of interfacial region 116, here at region 120A. This modified charge density within region 120A of 2DEG 120 changes the electrical behavior of an electronic device containing structure 100. FIGS. 2 and 6 illustrate, respectively, exemplary sensors 200 and 600, respectively, that incorporate the basic configuration and functionality of basic sensor structure 100 in the form of a high-electron-mobility transistor (HEMT) and a Schottky diode.

However, referring still to FIG. 1, the chemical process involving one or more constituents of environment 128 and catalyst 124 and the modification of the charge density is illustrated with respect to hydrogen-containing constituents, such as $H_2$ gas and various alkane gases having the chemical structure $C_xH_y$. Hydrogen-containing constituents such as these are of particular interest due to their presence in many industrial environments, some examples of which are provided below. When catalyst 124 is composed of one or more suitable materials that are catalytic relative to hydrogen, for example, one or more metals such as platinum, palladium, nickel, iridium, etc., in the presence of $H_2$ the catalyst adsorbs and subsequently decomposes the $H_2$ into atomic hydrogen, $H_a$, which diffuses through the catalyst metal to the metal/semiconductor interface 132. When at interface 132, the atomic hydrogen $H_a$ interacts with the surface of second layer 108 to passivate the interfacial states present at the interface, which in turn modifies the charge density within 2DEG 120. Similarly, in the presence of an alkane the catalyst adsorbs and subsequently decomposes the alkane into atomic hydrogen $H_a$ and a hydrocarbon radical. When at interface 132, the atomic hydrogen $H_a$ interacts with the surface of second layer 108 to passivate the interfacial states present at the interface, which in turn modifies the charge density within 2DEG 120 at region 120A. Catalyst 124 can be a pure catalytic metal, but it can also be, for example, a catalytic alloy, such as an alloy of the metals mentioned above, or a heterostructure stack of multiple catalytic metals/alloys.

In a particular example of basic sensor structure 100 suitable for use with one or more hydrogen-containing constituents such as the ones discussed above, first layer 104 is GaN, second layer 108 is $Al_xGa_{1-x}N$, wherein x=0.05 to 1.00, having a thickness in a range of about 2 nm to about 200 nm, and catalyst 124 is platinum deposited in a thickness within a range of about 5 nm to about 100 nm.

In certain environments, reactive catalytic materials may cause industrial hazards due to the chemical reactions that they drive forward. To minimize such hazards, in some embodiments of basic sensor structure 100 the area of catalyst 124 is typically, though not necessarily, below 50 μm by 50 μm. Using such small amounts of the catalytic material(s) can significantly decrease the risk of industrial hazards. However, for further decreasing of such risk, one or more additional layers 136 can be provided over catalyst 124. Any such protective layer(s) must allow the analyte of interest to permeate its structure, since interaction of the analyte with the catalytic material(s) is needed to achieve the charge-density altering effect within 2DEG 120 described above. Examples of materials that have been shown to work for protective layer(s) 136 for hydrogen-containing analytes include, but are not limited to, Parylene, polytetrafluoroethylene, and polymethyl methacrylate. Other materials may also be suitable.

Exemplary Sensors and Measurement Circuitry

As mentioned above, the basic structure illustrated by basic sensor structure 100 of FIG. 1 can be incorporated into a number of electronic devices, such as transistors and diodes in which the varying charge density in the 2DEG 120 manifests as measurable responses. FIG. 2 illustrates a sensor 200 based on an HEMT 204 and incorporating sensor structure 100 of FIG. 1. Referring to FIG. 2, and also to FIG. 1, catalyst 124 of FIG. 1 functions as a gate 208 of HEMT 204, while first and second layers 104 and 108 provide the 2DEG channel 212 of the HEMT. HEMT 204 also includes a source/ohmic contact 216 and a drain/ohmic contact 220, which function, respectively, as the source and drain of the HEMT. All of the characteristics and exemplary dimensions of basic sensor structure 100 of FIG. 1 apply to sensor 200.

As mentioned above relative to the functioning of basic sensor structure 100, when the dissociated particles, such as the atomic hydrogen $H_a$ provided in the example of FIG. 1, from the constituent(s) (analyte(s)) of chemical environment 128 reach interface 132, they tend to modify the states originally present there, thereby causing a change in the charge density within the adjacent portion of 2DEG 120. In sensor 200 of FIG. 2, because catalyst 124 (FIG. 1) is located at/is part of gate 208, those particles cause a change in the charge density within 2DEG channel 212, which changes the conductivity of HEMT 204.

Figure 3:
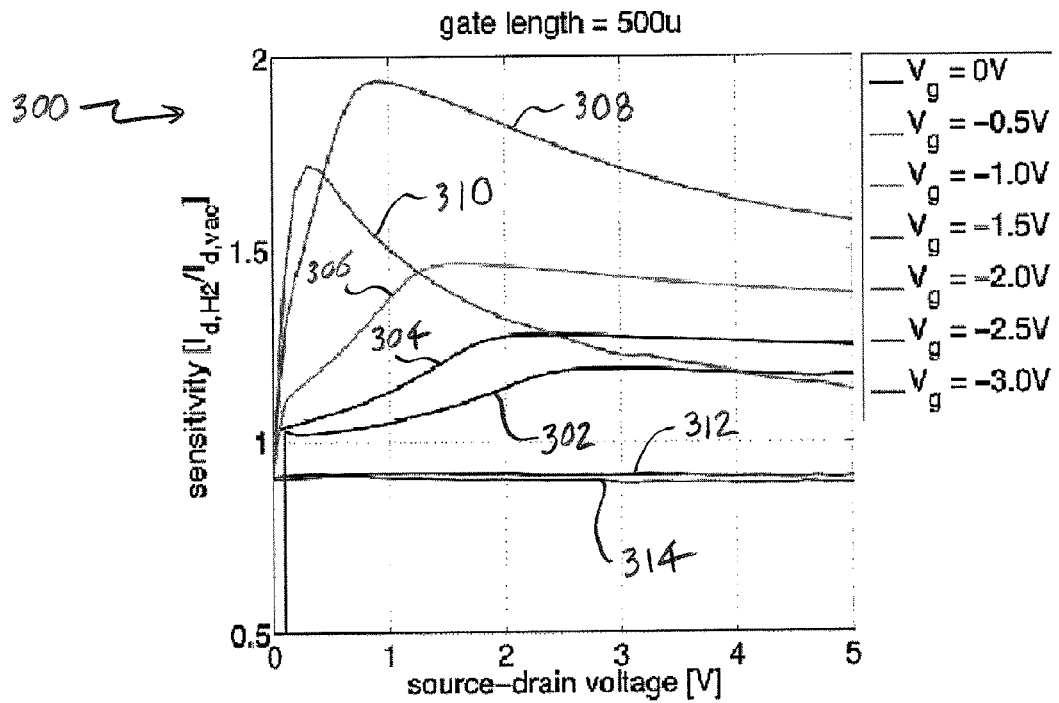
FIG. 3 is a graph of drain current sensitivity versus source-drain voltage for a particular example of the HEMT-based sensor of FIG. 2, showing current-sensitivity curves for several reverse gate bias voltages relative to $H_2$ gas at 25° C.

FIG. 3 shows a graph 300 that illustrates, in terms of sensitivity, the changes in conductivity of HEMT 204 due to the changes in the charge density within 2DEG channel 212 when a particular embodiment of sensor 200 is in the presence of $H_2$ and is configured to detect $H_2$, for example, as discussed above. In this particular example: first layer 104 was made of GaN; second layer 108 was a 60 nm thick layer of $AlGa_2N_2$; catalyst/gate 208 was a 500 μm wide by 500 μm long by 50 nm thick platinum layer; and each of source/ohmic contact 216 and drain/ohmic contact 220 were a 500 μm long by 50 nm thick titanium layer. In graph 300, the sensitivity of sensor 200 is defined as the ratio of the source-drain current measured in an H2 environment, $I_{d,H2}$, to the source-drain current measured in a vacuum, $I_{d,vac}$. As seen from sensitivity curves 302 to 314, testing revealed that the sensitivity of sensor 200 varies with the magnitude of the reverse-bias voltage applied to catalyst/gate 208.

Figure 4:
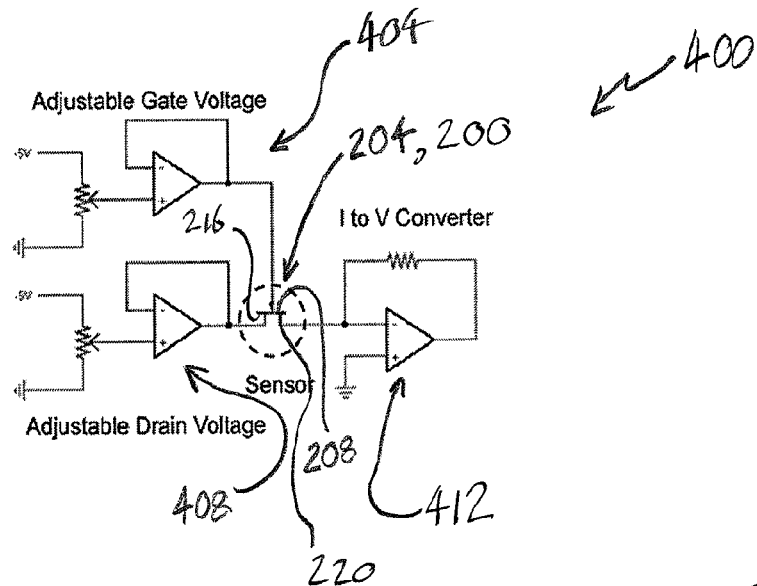
FIG. 4 is a schematic diagram of an HEMT-based sensor in a simple measurement circuit.

The change in conductivity of HEMT 204 can be sensed/measured using appropriate circuitry, such as the measurement circuitry 400 of FIG. 4. As seen in FIG. 4, measurement circuitry 400 includes: gate-voltage adjusting circuitry 404 for adjusting the reverse-bias voltage applied to catalyst/gate 208 of HEMT 204; drain voltage adjusting circuitry 408 for adjusting the voltage applied to source/ohmic contact 216 of HEMT 204; and a current-to-voltage converter 412 for converting the current from drain/ohmic contact 220 of HEMT 204 to a voltage that can be measured. Gate-voltage adjusting circuitry 404 and drain-voltage adjusting circuitry 408 allow sensor 200 to be tuned for the particular application at hand. As those skilled in the art will readily appreciate, sensor 200 and measurement circuitry 400 can be calibrated in a suitable manner so that a reference response can be obtained for use in detection algorithms.

Figure 5:
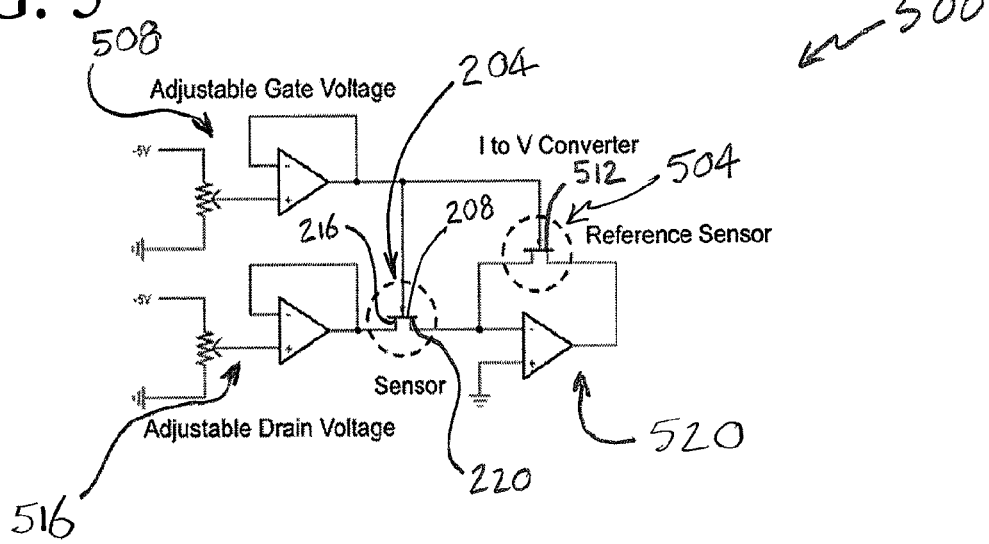
FIG. 5 is a schematic diagram of an HEMT-based sensor in a reference-type measurement circuit.

FIG. 5 illustrates alternative measurement circuitry 500 that utilizes a built-in reference HEMT 504 that is identical to HEMT 204 of sensor 200, but is not exposed to the chemical environment containing the target analyte(s) (constituent(s)) of the chemical environment. Measurement circuitry 500 is similar to measurement circuitry 400 of FIG. 4 in that it also contains gate-voltage adjusting circuitry 508 for adjusting the reverse-bias voltage applied to catalyst/gate 208 of HEMT 204 and the like catalyst/gate 512 of reference HEMT 504; drain voltage adjusting circuitry 516 for adjusting the voltage applied to source/ohmic contact 216 of HEMT 204; and a current-to-voltage converter 520 for converting the current from drain/ohmic contact 220 of HEMT 204 to a voltage that can be measured. Built-in reference sensor 504 avoids the need for the calibration used for measurement circuitry 400 of FIG. 4. As those skilled in the art will readily appreciate, measurement circuitries 400 and 500 are simply provided as examples, and other measurement circuitry can be used in the alternative. Those skilled in the art will understand how to design alternative circuitry using known techniques.

FIG. 6 illustrates a sensor 600 based on a Schottky diode 604 and incorporating sensor structure 100 of FIG. 1. Referring to FIG. 6, and also to FIG. 1, catalyst 124 of FIG. 1 functions as a Schottky contact 608 of Schottky diode 604, while first and second layers 104 and 108 provide the 2DEG 612 of the diode. HEMT 204 also includes an ohmic contact 616. As those skilled in the art will readily understand, with this arrangement, contacts 608 and 612 can function as the plates of a capacitor. All of the characteristics and exemplary dimensions of basic sensor structure 100 of FIG. 1 apply to sensor 200.

As mentioned above relative to the functioning of basic sensor structure 100, when the dissociated particles, such as the atomic hydrogen $H_a$ provided in the example of FIG. 1, from the constituent(s) (analyte(s)) of chemical environment 128 reach interface 132, they tend to passivate the states originally present there, thereby causing a change in the charge density within the adjacent region 120A of 2DEG 120. In sensor 600 of FIG. 6, because catalyst 124 is located at/is part of Schottky contact 612, those particles cause a change in the charge density within 2DEG 612, which changes the capacitance of Schottky diode 604.

Figure 7:
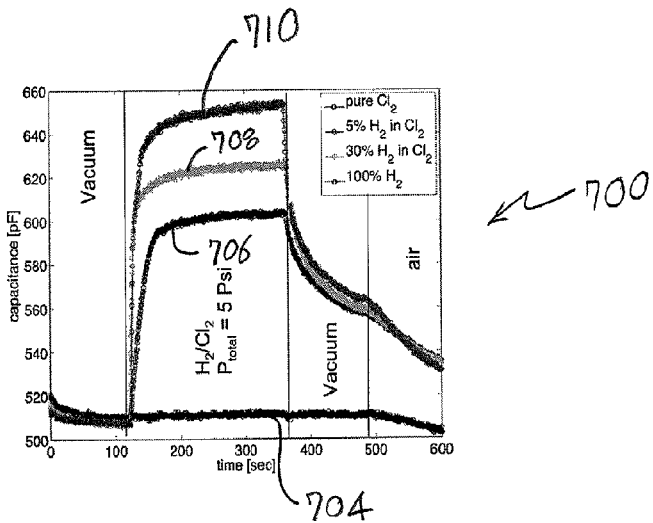
FIG. 7 is graph of capacitance versus time for a particular example of the Schottky-diode-based sensor of FIG. 6, showing capacitance for several concentrations and mixtures of $H_2$ gas at 25° C.

FIG. 7 shows a graph 700 that illustrates the changes in capacitance of Schottky diode 604 due to the changes in charge density within 2DEG 612 when a particular embodiment of sensor 600 is in an environment with and without $H_2$ and is configured to detect $H_2$, for example as discussed above. In this particular example, first layer 104 was made of GaN; second layer 108 was a 60 nm thick layer of $AlGa_7N_2$; Schottky contact/catalyst 608 was a 500 μm wide by 500 μm long by 25 nm thick platinum layer; and ohmic contact 616 was a 500 μm long by 50 nm thick titanium layer. Curves 704, 706, 708, 710 were generated by subjecting the exemplary embodiment of sensor 600 first to a vacuum for about 120 seconds, then subjecting the sensor to $H_2$ or $Cl_2$ or a combination of the two at a pressure of about 5 psi for about 250 seconds, then subjecting the sensor to a vacuum for about 120 seconds, and finally subjecting the sensor to air. As seen by curves 706, 708, 710, sensor 600 reacts quickly to the $H_2$, and the amount of capacitance increases with increasing concentrations of $H_2$. Curve 704 shows that sensor 600 is not sensitive to $Cl_2$, which foretells its usefulness in detecting hydrogen gas in chlorine environments, as discussed below in detail.

Figure 8:
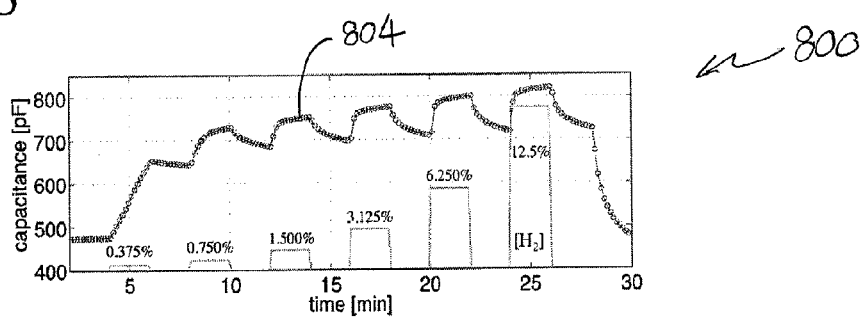
FIG. 8 is a graph of capacitance versus time illustrating the quick response time of a particular example of the Schottky-diode-based sensor of FIG. 6, showing the sensor's response to increasing levels of $H_2$ concentration over time.

FIG. 8 shows a graph 800 of capacitance versus time for a particular example of Schottky-diode-based sensor 600 of FIG. 6. Curve 804 was generated by alternatingly exposing sensor 600 to pure $N_2$ and combinations of $N_2$ and $H_2$ containing differing amounts of $H_2$, as represented in graph 800 as a volume percentage of $H_2$ and ranging from 0.375% to 12.5%. As can be readily seen from curve 804, sensor 600 reacts quickly (capacitance rises) when the $H_2$ is present, while the capacitance drops more slowly during the intervals of exposure to only $N_2$. As is also seen, the capacitance increases with increasing concentrations of $H_2$.

Figure 9:
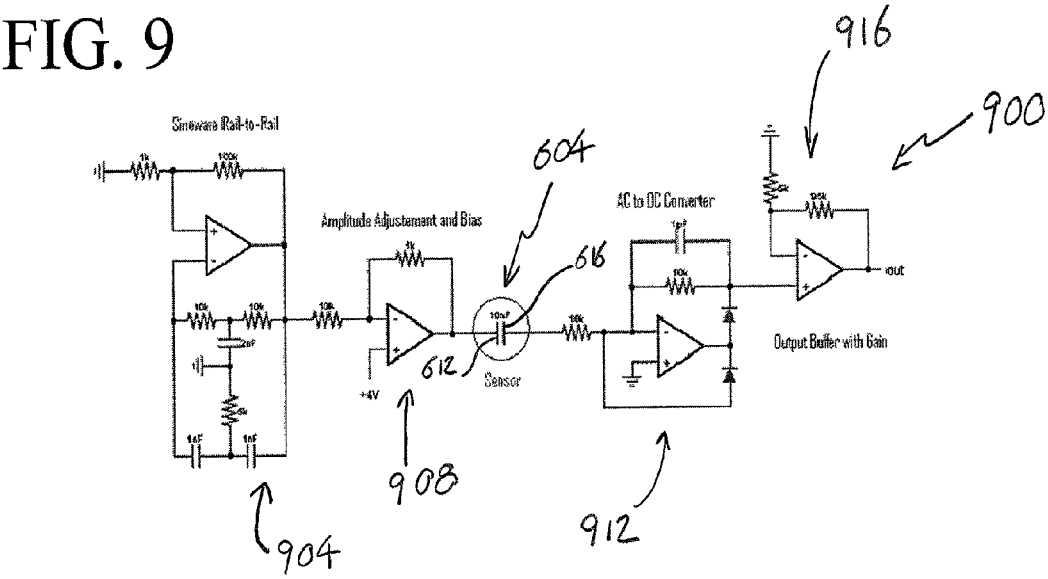
FIG. 9 is a schematic diagram of a Schottky-diode-based sensor in a measurement circuit.

The change in capacitance of Schottky diode 604 can be sensed/measured using appropriate circuitry, such as the measurement circuitry 900 of FIG. 9. As seen in FIG. 9, measurement circuitry 900 includes: a rail-to-rail sinewave generator 904; amplitude adjustment and bias circuitry 908 coupled between the sinewave generator and one of the contacts (plates) 612 and 616 of Schottky diode 604; an AC-to-DC converter 912 coupled to the opposite contact (plate) of the Schottky diode; and output buffer and gain circuitry 916 electrically coupled to the AC-to-DC converter as shown. Those skilled in the art will readily appreciate that measurement circuitry 900 is simply provided as an example and that other measurement circuitry can be used in the alternative. Those skilled in the art will understand how to design alternative circuitry using known techniques.

Exemplary Systems and Applications

Figure 10:
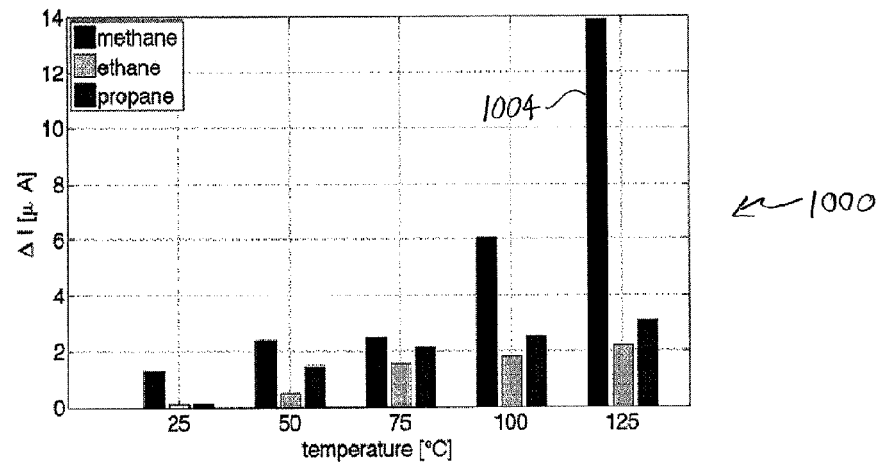
FIG. 10 is a graph of current change versus temperature for an HEMT-based sensor, showing the sensor's response to methane, ethane, and propane at several temperatures.

Catalytic materials used for catalyst 124 of basic sensor structure 100 of FIG. 1 can have differing catalytic efficiencies at differing temperatures toward differing hydrocarbons. An example of this for platinum used as catalyst 124 is illustrated in FIG. 10 relative to methane, ethane, and propane for the temperatures 25° C., 50° C., 75° C., 100° C., and 125° C. FIG. 10 is a graph 1000 of change in current through an HEMT-based sensor containing basic sensor structure 100 of FIG. 1, such as sensor 200 of FIG. 2, in which the catalyst is platinum. As seen in FIG. 10, the sensitivity of the sensor to methane, indicated by bar 1004, as measured by the change in current through the HEMT-based sensor, is generally much greater throughout the entire temperature range shown, with the sensitivity being the greatest at 125° C. While the sensitivity of the sensor to ethane and propane does increase with increasing temperature, the increases are not at the rate of methane.

Through experimentation with the sensor used to create graph 1000 of FIG. 10, it was seen that the response signal of the sensor is an agglomeration, sometimes the sum, of the signals in the same amount of each of the pure hydrocarbons. This fact can be leveraged to create sensor systems that can distinguish between two or more analytes in a chemical environment to which the sensor is responsive. For example, a simple sensor system for determining whether a particular chemical environment contains methane when that environment could contain any one or more of methane, ethane, and propane might include a pair of HEMT-based sensors, such as two of sensors 200 of FIG. 2, in which one of the sensors is operated at 75° C. and the other is simultaneously operated at 125° C. Because the two sensors are simultaneously exposed to the same environment, when methane is present, the sensor operated at 125° C. will experience a much greater change in current, as seen in graph 1000 of FIG. 10. This response can be used with suitable logic (not shown) to indicate the presence of methane.

Figure 11:
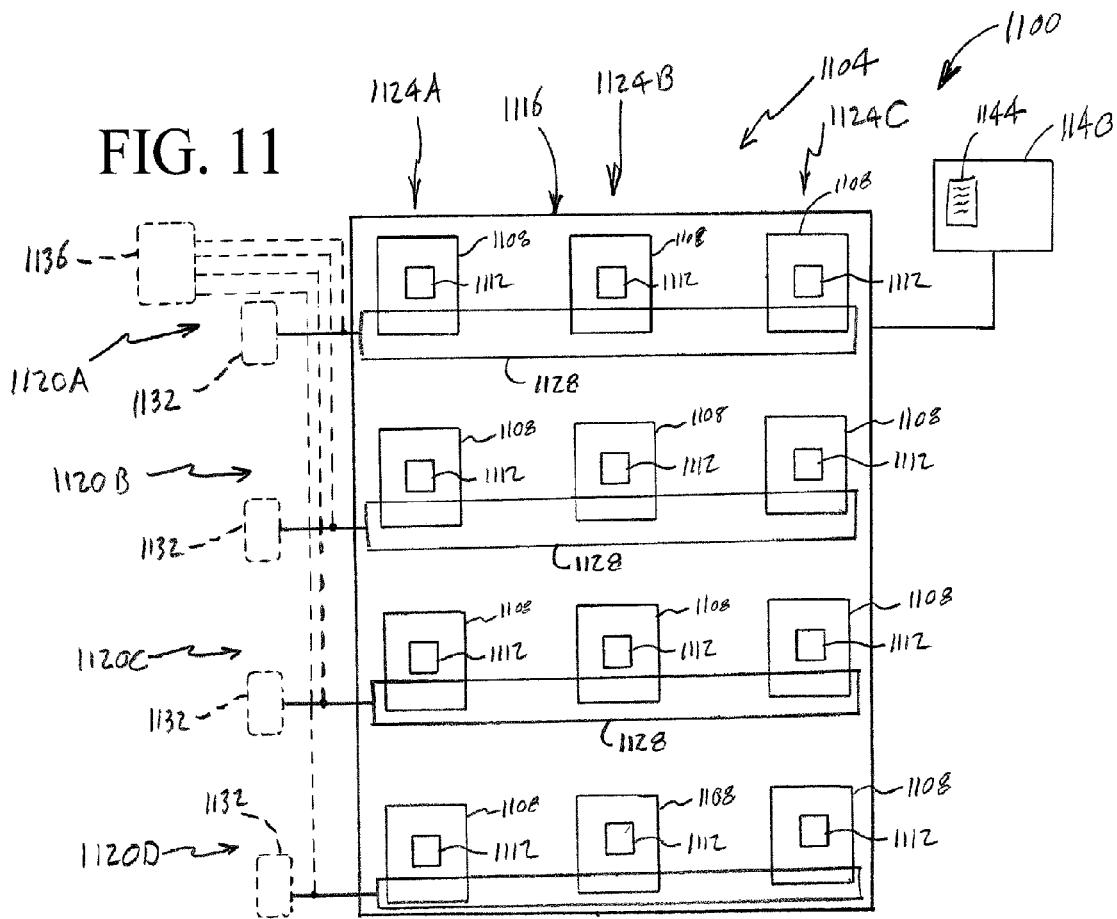
FIG. 11 is a schematic diagram of a sensor system configured for distinguishing analytes from one another.

While that example was simple, much more complex sensor systems can be made. For example, FIG. 11 illustrates a sensor system 1100 that includes an array 1104 of sensors 1108 each having basic sensor structure 100 of FIG. 1 and including a catalyst 1112. Each sensor 1108 can be, for example, an HEMT-based sensor, such as sensor 200 of FIG. 2, or a Schottky-diode-based sensor, such as sensor 600 of FIG. 6. In this example, differing sensors 1108 (FIG. 11) are not only operated at differing temperatures during deployment, but the sensors also have catalysts 1112 of differing catalyst materials. For example, the sensors can be arranged in a matrix 1116 having rows 1120A-D and columns 1124A-C. In one embodiment, sensors 1108 in each row 1120A-D are operated at a constant temperature, but with the temperature being different from row to row. Similarly, sensors 1108 in each column 1124A-C have a common catalyst material, but the material differs from column to column. In order to control the temperature, each sensor 1108 or an entire row 1120A-D or other portion thereof includes a temperature control system 1128, which can include either a heater or a cooler, or both, as needed to keep the sensors at the desired temperature. Each temperature control system 1128 can be locally controlled by a local controller 1132 or globally controlled by a global controller 1136.

Figure 12:
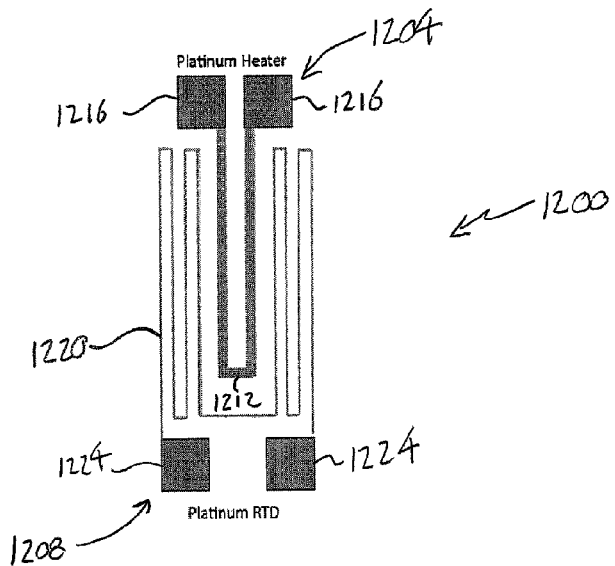
FIG. 12 is a diagram of a heating system that can be used with sensors in the sensor system of FIG. 11.

An example of a suitable heating system 1200 that could be used for one or more of temperature control systems 1128 is shown in FIG. 12. As seen in FIG. 12, heating system 1200 includes a resistive current heater 1204 and a resistive temperature detector (RTD) 1208, each in any suitable configuration for achieving the desired heating. In one example, heater 1204 includes a heating element 1212 made of platinum and pads 1216 made of gold. Pads 1216 are electrically connected to a power supply (not shown). Similarly, in this example RTD 1208 comprises a resistance element 1220 made of platinum and a pair of pads 1224 made of gold. Pads 1224 are electrically coupled to a proportional-integral-derivative (PID) controller (not shown). During operation, electrical current is passed through heater 1204 causing heating element 1212 to heat up, thereby increasing the temperature of the sensor (not shown) thermally coupled to the heater and increasing the resistance in resistance element 1220 of RTD 1208, which is operated at a lower current than the heater to avoid self heating. The PID controller uses the current measured using RTD 1208 to control the current supplied to heater 1204. In a specific example, pads 1216 and 1224 are 100 µm by 100 µm in size. While platinum is used for the disclosed example, those skilled in the art will readily appreciate that another conductive material, such as nickel and graphite, can be used, while materials with strong thermal dependence on resistivity are particularly useful. In the case of a cooling system being needed for temperature control, a thermoelectric cooling device (not shown) or other suitable cooling device can be used.

Referring back to FIG. 11, sensor system 1100 also includes a matrix analyzer 1140 designed and configured to perform a matrix analysis on the individual responses of sensors 1108 within matrix 1116 to determine the identity(ies) and/or quantity(ies) of one or more analytes of interest. As those skilled in the art will readily appreciate, the catalyst material(s) and/or temperatures, as well as the number of sensors 1108, used in array 1104 can be carefully selected for a particular application. Similarly, the algorithm 1144 used by matrix analyzer 1140 can be carefully tailored to analyze the expected sensor responses in a manner that one or more particular analytes can be identified out of a range of possible analytes and/or one or more amounts of one or more analytes can be quantified. In one example, the analytes of interest consist of methane and ethane in a mixture. By designing a sensor system 1100 using two sensors each operated at differing temperatures and using FIG. 10 and a matrix analyzer 1140, the quantitative determination of the methane and ethane concentrations can be accomplished. The simplest process is to have one sensor operate at 25° C. and the other at 75° C. As can be seen in FIG. 10, the sensor response is almost entirely methane at 25° C. From this signal, the concentration at 25° C. can be measured. Using the concentration, the methane signal at 75° C. can be determined using FIG. 10, and the ethane concentration can be calculated using the measured signal at 75° C. and the determined methane signal. Those skilled in the art will be able to increase accuracy and precision using more sensors for this binary case and extrapolate this binary case to additional sensors with more analyte gases.

Figure 13:
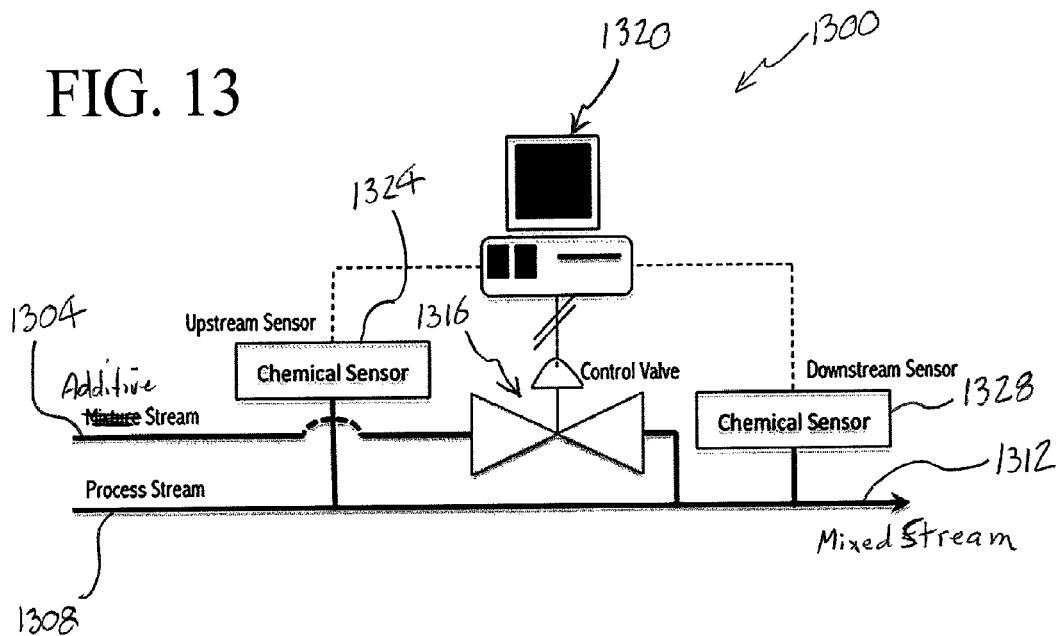
FIG. 13 is a schematic diagram of a process containing a sensor-based mixture control system made in accordance with aspects of the present invention.
Figure 14:
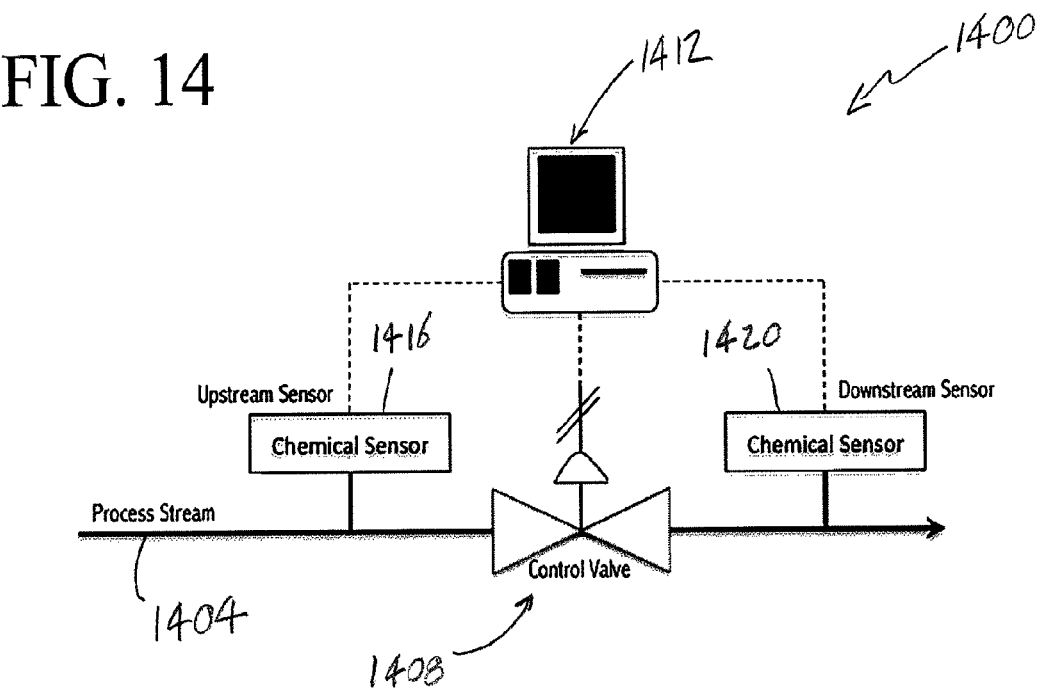
FIG. 14 is a schematic diagram of a process containing a sensor-based flow control system made in accordance with aspects of the present invention.
Figure 15:
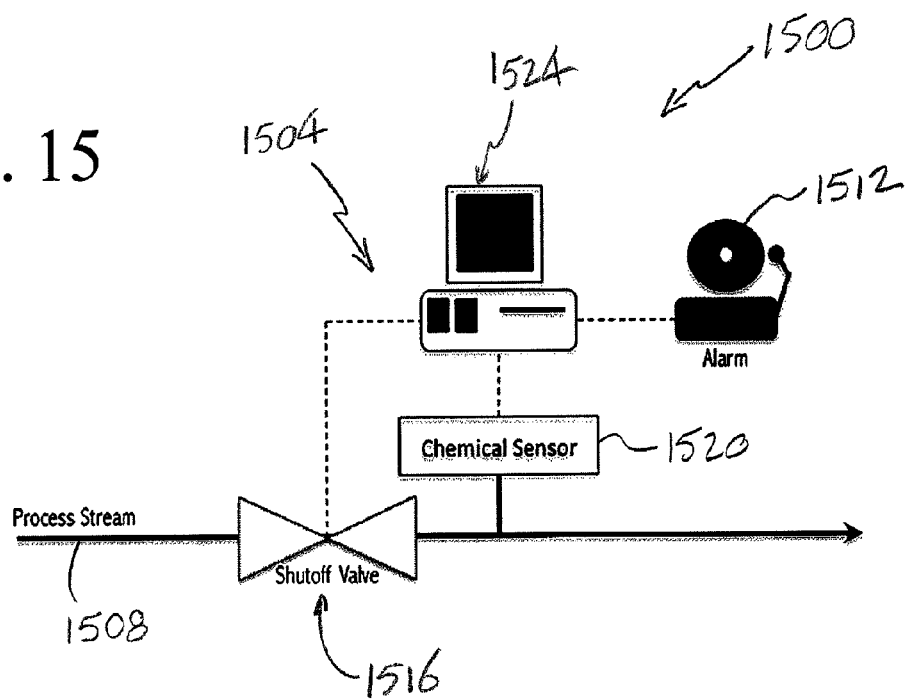
FIG. 15 is a schematic diagram of a process containing a sensor-based alarm system made in accordance with aspects of the present invention.

Sensors and sensor systems made in accordance with various aspects of the present disclosure can be deployed into many different applications for a variety of purposes. Examples of applications for severe environment chemical sensors described herein include process control and safety applications. Examples of these applications are illustrated in FIGS. 13 to 15.

Process control applications can be divided into mixture-control applications and flow-control applications. In an exemplary mixture control application, one or more sensors are deployed in a process upstream and/or downstream of a control device in a first stream that combines with a second stream, and the sensor(s) output(s) are used to control the combining of the process streams. FIG. 13 illustrates such a process 1300. In process 1300, an additive stream 1304 is combined with a process stream 1308 to create a mixed stream 1312. In this example, process stream 1308 includes a hydrogen-containing gas in an amount that can be less than the desired amount in the mixed stream. Consequently, process 1300 involves adding more of the hydrogen containing gas to process stream 1308 as needed via additive stream 1304. To facilitate this, process 1300 includes an automatedly controlled valve 1316 that controls the amount of additive stream 1304 delivered to process stream 1308 in order to increase the amount of hydrogen-containing gas in process stream 1308. Valve 1316 is controlled by a machine 1320, such as a computer, dedicated controller, etc., that utilizes responses of an upstream sensor 1324 that monitors the amount of the hydrogen-containing gas in process stream 1308 and a downstream sensor 1328 that monitors the amount of the hydrogen gas in mixed stream 1312.

Upstream and downstream sensors 1324 and 1328 each contain one or more electronic devices that utilize basic sensor structure 100 of FIG. 1, such as HEMT-based devices and Schottky-diode-based devices. For example, each HEMT-based device can be the HEMT-based sensor 200 of FIG. 2 configured for sensing the presence of hydrogen, and each Schottky-diode-based device can be the Schottky-based sensor 600 of FIG. 6 configured for sensing the presence of hydrogen. Of course, sensors 1324 and 1328 of FIG. 13 can include temperature control systems, such as systems 1128 described above in connection with sensor system 1100 of FIG. 11, as needed for the particular application at issue. Machine 1320 executes an algorithm that uses the responses of sensors 1324 and 1328 to control valve 1316 and the amount of hydrogen-containing gas in additive stream 1304 delivered to process stream 1308. Such algorithms, other than the use of the responses of the unique sensors 1324 and 1328 taught in this disclosure, are known and can be implemented by those of ordinary skill in the art.

An example of this type of mixture control is the control of fuel delivered to turbines. For example, changes in the energy content of natural gas, which typically vary based upon the geography of extraction, require differing amounts of oxygen for maximum energy generation. Real-time measure of the hydrocarbon (methane, ethane, propane, and butane) concentration within the fuel stream allow for real-time adjustments to the oxygen flow rate and the combustion conditions to be constantly optimized. The elevated temperature within the turbine requires the severe environment sensors detailed herein. Those skilled in the art will understand that there are many other mixture-control applications for sensors taught herein.

In an exemplary flow-control application, one or more sensors are deployed upstream and/or downstream of a flow-control device in a process stream, and the sensor(s) output(s) are used to control the flow of the process stream. FIG. 14 illustrates such a process 1400. In process 1400, a process stream 1404 flows to a downstream part (not shown) of the process that requires modulation of the process stream based on the amount of one or more hydrogen-containing gases in the process stream. To effect this modulation, process 1400 includes an automatedly controlled valve 1408 for modulating the flow of process stream 1404. Valve 1408 is controlled by a machine 1412, such as a computer, dedicated controller, etc., that utilizes responses of an upstream sensor 1416 that monitors the amount of the hydrogen-containing gas in process stream 1404 and/or a downstream sensor 1420 that also monitors the amount of the hydrogen-containing gas in the process stream.

Upstream and downstream sensors 1416 and 1420 each contain one or more electronic devices that utilize basic sensor structure 100 of FIG. 1, such as HEMT-based devices and Schottky-diode-based devices. For example, each HEMT-based device can be the HEMT-based sensor 200 of FIG. 2 configured for sensing the presence of hydrogen, and each Schottky-diode-based device can be the Schottky-based sensor 600 of FIG. 6 configured for sensing the presence of hydrogen. Of course, sensors 1416 and 1420 of FIG. 14 can include temperature control systems, such as systems 1128 described above in connection with sensor system 1100 of FIG. 11, as needed for the particular application at issue. Machine 1412 executes an algorithm that uses the responses of sensor 1416 and/or sensor 1420 to control valve 1408 and the rate at which process stream 1404 is delivered downstream. Such algorithms, other than the use of the responses of the unique sensors 1416 and 1420 taught in this disclosure, are known and can be implemented by those of ordinary skill in the art.

In a safety application, one or more sensors are deployed into a process, and the sensor(s) output(s) are used to control an alarm and/or initiate shutting down the process, shutting off a process stream, and/or taking any other action to rectify the situation and avoid a catastrophic event. FIG. 15 illustrates a process 1500 that utilizes a safety system 1504. In process 1500, a process stream 1508 should not contain a hydrogen-containing gas over a certain amount, including none. If the threshold is exceeded in this embodiment, safety system 1504 sounds an alarm and shuts off the flow of process stream 1508. To effect these actions, safety system 1504 includes an alarm device 1512, automatedly controlled shutoff valve 1516, a sensor 1520, and a machine 1524, such as a computer, dedicated controller, etc., that utilizes the response of the sensor to control the alarm and shutoff valve.

Sensor 1520 contains one or more electronic devices that utilize basic sensor structure 100 of FIG. 1, such as HEMT-based devices and Schottky-diode-based devices. For example, each HEMT-based device can be the HEMT-based sensor 200 of FIG. 2 configured for sensing the presence of hydrogen, and each Schottky-diode-based device can be the Schottky-based sensor 600 of FIG. 6 configured for sensing the presence of hydrogen. Of course, sensor 1520 of FIG. 15 can include temperature control systems, such as systems 1128 described above in connection with sensor system 1100 of FIG. 11, as needed for the particular application at issue. Machine 1524 executes an algorithm that uses the responses of sensor 1520 to control alarm device 1512 and shutoff valve 1516 based on the level of hydrogen-containing gas in process stream 1508 exceeding the preset threshold. Such algorithms, other than the use of the responses of the unique sensor 1520 taught in this disclosure, are known and can be implemented by those of ordinary skill in the art. One potential example of a safety application is the detection of hydrogen within a chlor-alkali environment. The extreme corrosiveness of the environment requires the severe-environment sensors detailed herein. Upon detection of hydrogen within the chlor-alkali stream, the safety system can initiate shut-off of the electrolytic cells and alert a plant worker to the shut down.

It is noted that configurations having valves are shown in FIGS. 13 to 15 for simplicity and as a concrete example of one possible deployment set-up. In actuality, machines 1320, 1412, and 1524 may perform any number of feedback driven actions based upon the sensor signal(s). Examples include modulate temperature, pressure, shut-off electrical systems, input additional gases/fluids, etc.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A sensor system for sensing a constituent of a chemical environment, wherein the constituent is a member of a chemical family, the sensor system comprising:
an array of sensors arranged in a matrix, said array of sensors designed, configured, and selected to sense multiple member chemicals of the chemical family and having differing sensitivities to differing ones of the multiple member chemicals based on sensor temperature; wherein each of said sensors includes a catalyst and one or more additional layers designed and configured to protect said catalyst and to allow the constituent to permeate through to said catalyst; wherein said array of sensors includes two-dimensional electron gas (2DEG) sensors;
a plurality of heaters having a plurality of heating elements located proximate to corresponding respective ones of said sensors;
a temperature control system operatively connected to said plurality of heating elements and designed and configured to maintain, simultaneously, differing ones of said sensors in said matrix at differing temperatures below 200° C. during sensing operations of the sensor system;
a sensor response system operatively coupled to said sensors and designed and configured to measure responses of said sensors; and
a matrix analyzer containing an algorithm designed and configured to analyze responses of said sensors, operating at differing temperatures, measured by said sensor response system and to determine the presence of the constituent and distinguish the constituent from the rest of the multiple member chemicals.

2. A sensor system according to claim 1, wherein the chemical family is hydrocarbons and said 2DEG sensors have responses sensitive to hydrogen.

3. A sensor system according to claim 2, wherein the chemical family is hydrocarbons with the chemical formula of $C_xH_y$.

4. A sensor system according to claim 1, wherein each of said 2DEG sensors comprises a high-electron-mobility transistor (HEMT).

5. A sensor system according to claim 4, wherein each said HEMT has a gate electrode that provides said catalyst, and said catalyst is provided for stripping atomic hydrogen from the constituent.

6. A sensor system according to claim 1, wherein each of said 2DEG sensors comprises a Schottky diode.

7. A sensor system according to claim 6, wherein each said Schottky diode has a Schottky electrode that provides said catalyst, and said catalyst is provided for stripping atomic hydrogen from the constituent.

8. A sensor system according to claim 1, wherein each said catalyst is designed and configured to react with the constituent so as to change an electrical response of the corresponding one of said sensors.

9. A sensor system according to claim 8, wherein said one or more additional layers includes a material that covers said catalyst, is inert to the chemical environment, and has been selected to permit the constituent to reach said catalyst.

* * * * *